United States Patent
Suzuki et al.

(10) Patent No.: US 10,420,625 B2
(45) Date of Patent: Sep. 24, 2019

(54) VIBRATION DETECTION MODULE, VIBRATION DETECTION METHOD, AND SURGICAL SYSTEM

(71) Applicant: SONY CORPORATION, Tokyo (JP)

(72) Inventors: Hiroyuki Suzuki, Tokyo (JP); Kenichiro Nagasaka, Tokyo (JP); Masaya Kinoshita, Saitama (JP); Tomoki Tamada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/554,013

(22) PCT Filed: May 13, 2016

(86) PCT No.: PCT/JP2016/002368
§ 371 (c)(1),
(2) Date: Aug. 28, 2017

(87) PCT Pub. No.: WO2016/189819
PCT Pub. Date: Dec. 1, 2016

(65) Prior Publication Data
US 2018/0071047 A1  Mar. 15, 2018

(30) Foreign Application Priority Data

May 25, 2015 (JP) ................................ 2015-105241

(51) Int. Cl.
*G08B 21/00* (2006.01)
*A61B 90/00* (2016.01)
(Continued)

(52) U.S. Cl.
CPC .............. *A61B 90/06* (2016.02); *A61B 17/29* (2013.01); *A61B 34/20* (2016.02); *A61B 34/25* (2016.02);
(Continued)

(58) Field of Classification Search
CPC ......... A61B 34/30; A61B 34/20; A61B 34/76; G08B 21/00
See application file for complete search history.

(56) References Cited

U.S. PATENT DOCUMENTS 4,655,673 A    4/1987  Hawkes
2001/0039419 A1  11/2001 Francischelli et al.
(Continued)

FOREIGN PATENT DOCUMENTS

EP    0 125 895 A1    11/1984
JP    59-209797       11/1984
(Continued)

OTHER PUBLICATIONS

International Search Report dated Oct. 31, 2016 in PCT/JP2016/002368 filed May 13, 2016.
(Continued)

*Primary Examiner* — Phung Nguyen
(74) *Attorney, Agent, or Firm* — Oblon, McClelland, Maier & Neustadt, L.L.P.

(57) ABSTRACT

There is provided a medical apparatus, including medical vibration detection circuitry that is detachable from a medical instrument at an attachment position of the medical instrument in a longitudinal direction and that is configured to detect vibration generated in a distinct portion of the medical instrument, the distinct portion including at least a portion disposed toward a distal end of the medical instrument from the attachment position.

23 Claims, 6 Drawing Sheets

(51) Int. Cl.
*A61B 90/50* (2016.01)
*A61B 34/37* (2016.01)
*A61B 34/00* (2016.01)
*A61B 34/20* (2016.01)
*A61B 17/29* (2006.01)
*A61B 17/00* (2006.01)
*A61B 18/00* (2006.01)

(52) U.S. Cl.
CPC .............. *A61B 34/37* (2016.02); *A61B 34/76* (2016.02); *A61B 90/50* (2016.02); *A61B 2017/00075* (2013.01); *A61B 2017/00115* (2013.01); *A61B 2018/0088* (2013.01); *A61B 2018/00303* (2013.01); *A61B 2034/2048* (2016.02); *A61B 2034/2063* (2016.02); *A61B 2090/064* (2016.02); *A61B 2090/065* (2016.02)

(56) References Cited

U.S. PATENT DOCUMENTS

| | | | |
|---|---|---|---|
| 2002/0120188 A1* | 8/2002 | Brock | A61B 5/0086 600/407 |
| 2004/0186465 A1 | 9/2004 | Francischelli et al. | |
| 2007/0118107 A1 | 5/2007 | Francischelli et al. | |
| 2012/0143182 A1* | 6/2012 | Ullrich | A61B 18/1445 606/45 |
| 2012/0310257 A1* | 12/2012 | Kuchenbecker | A61B 34/30 606/130 |
| 2015/0272575 A1* | 10/2015 | Leimbach | A61B 17/072 227/175.3 |
| 2016/0030119 A1* | 2/2016 | Devengenzo | A61B 34/37 606/130 |
| 2017/0189127 A1* | 7/2017 | Weir | A61B 34/32 |

FOREIGN PATENT DOCUMENTS

| | | |
|---|---|---|
| JP | 08-117228 A | 5/1996 |
| JP | 10-094512 A | 4/1998 |
| JP | 2013-169619 | 9/2013 |

OTHER PUBLICATIONS

Office Action dated Apr. 16, 2019, in Japanese Patent Application No. 2015-105241. (10 pgs.).

* cited by examiner

[Fig. 1]
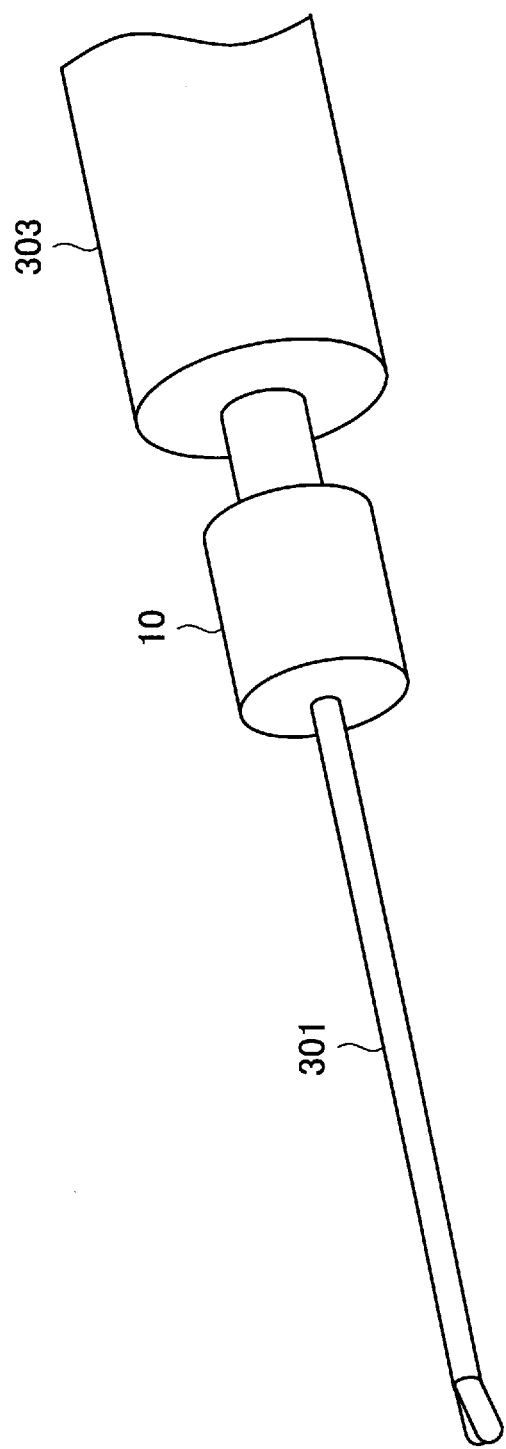

[Fig. 2]
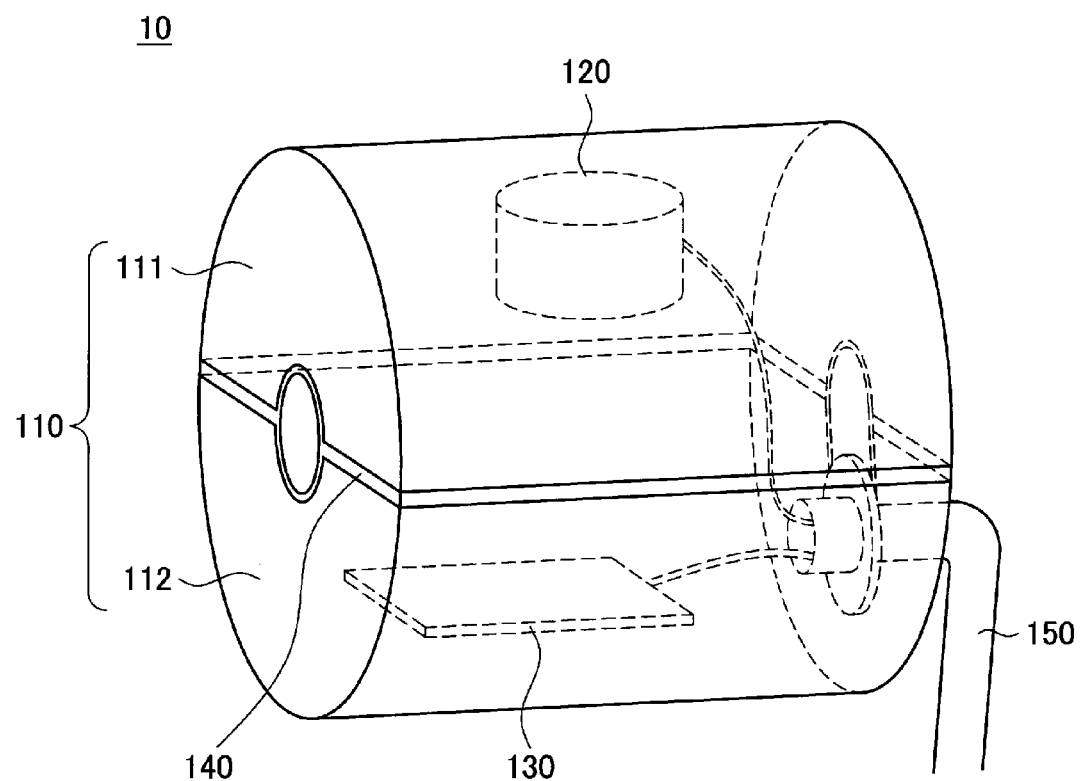

[Fig. 3]
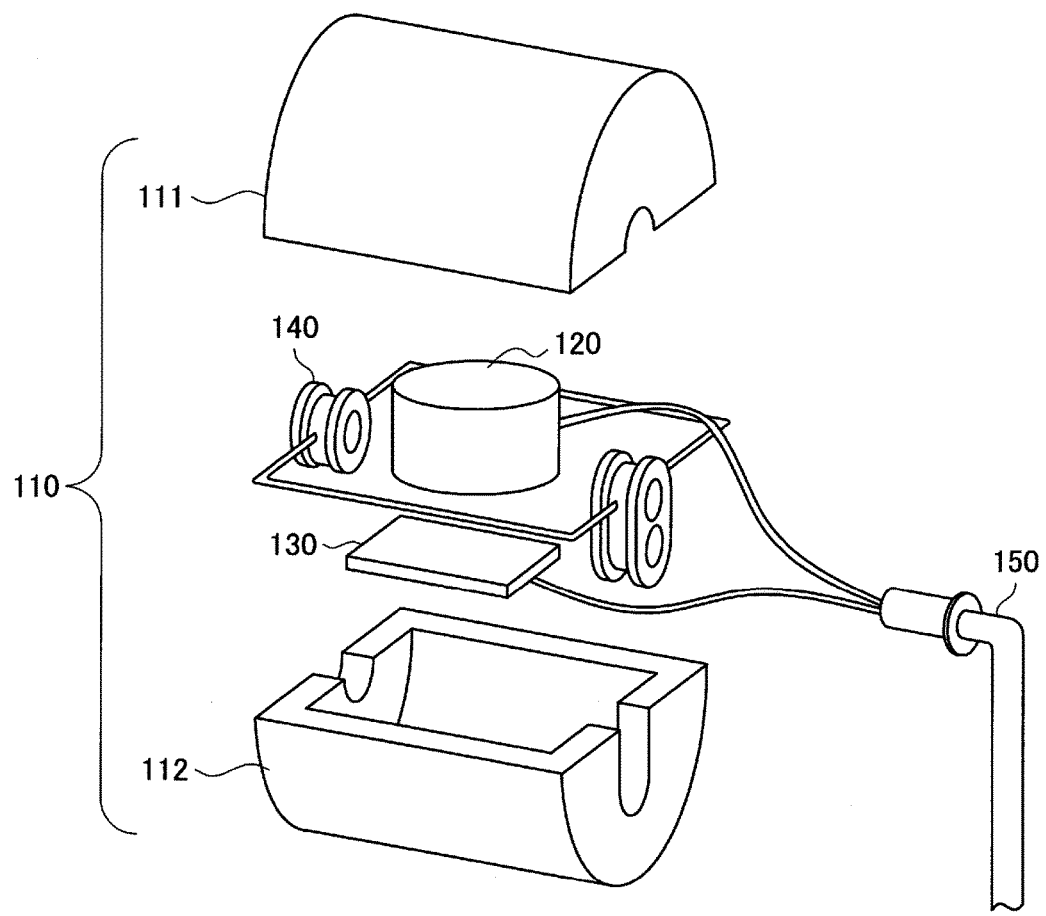

[Fig. 4]
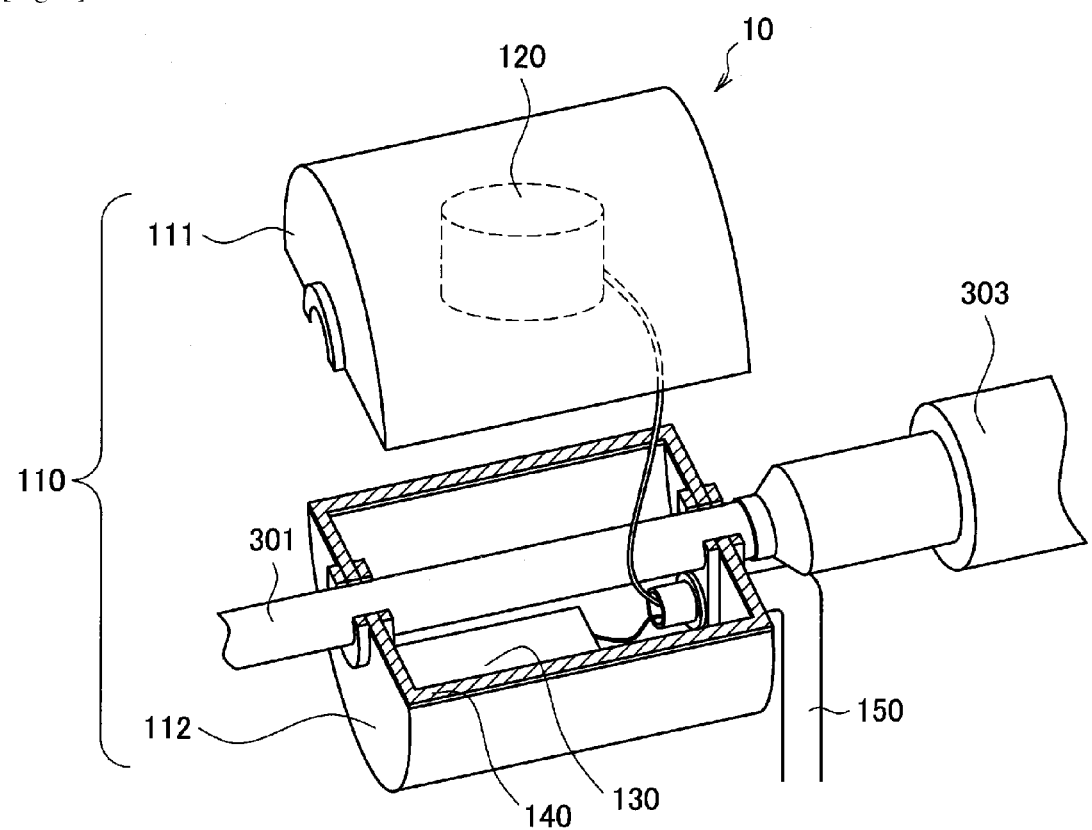

[Fig. 5]
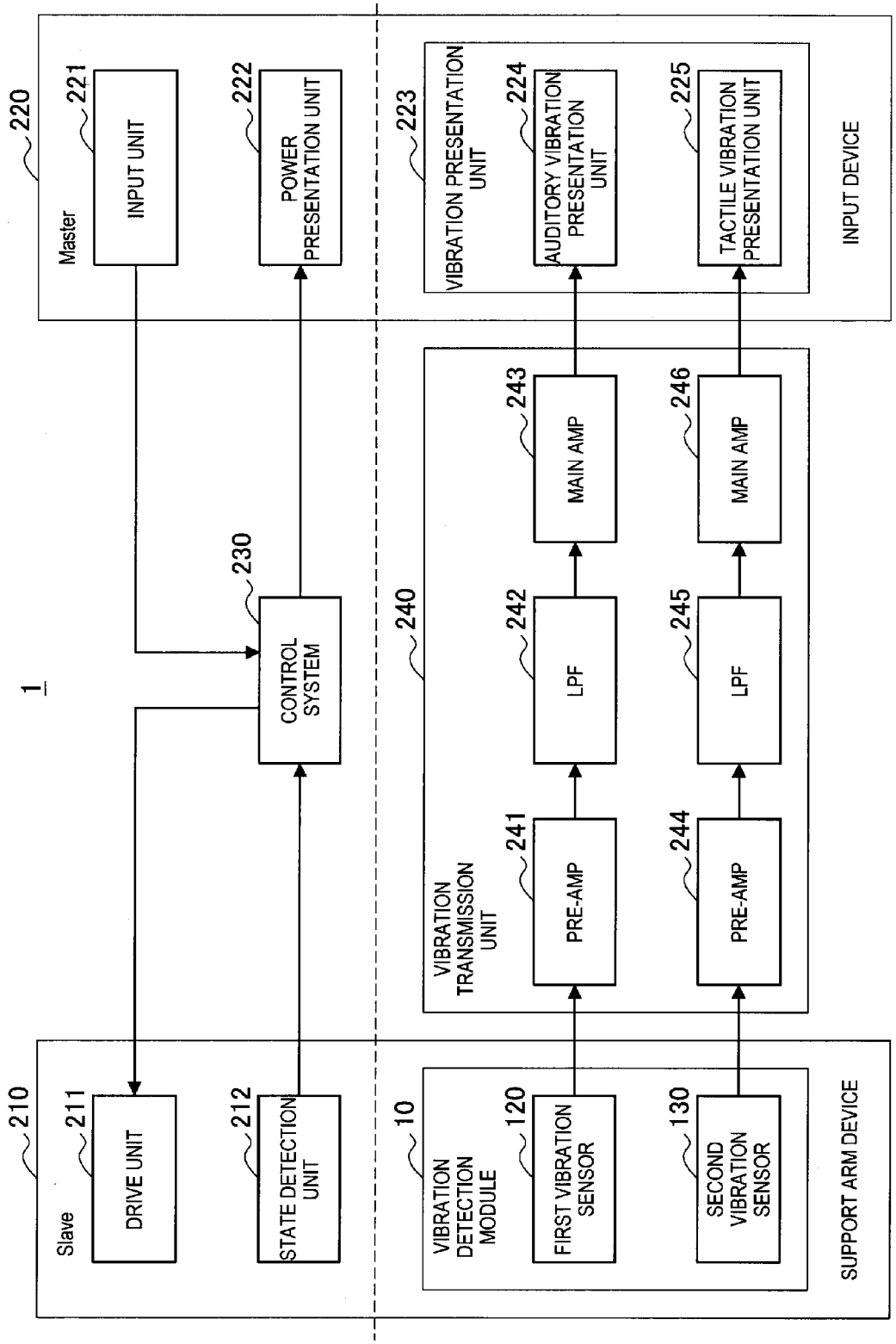

[Fig. 6]
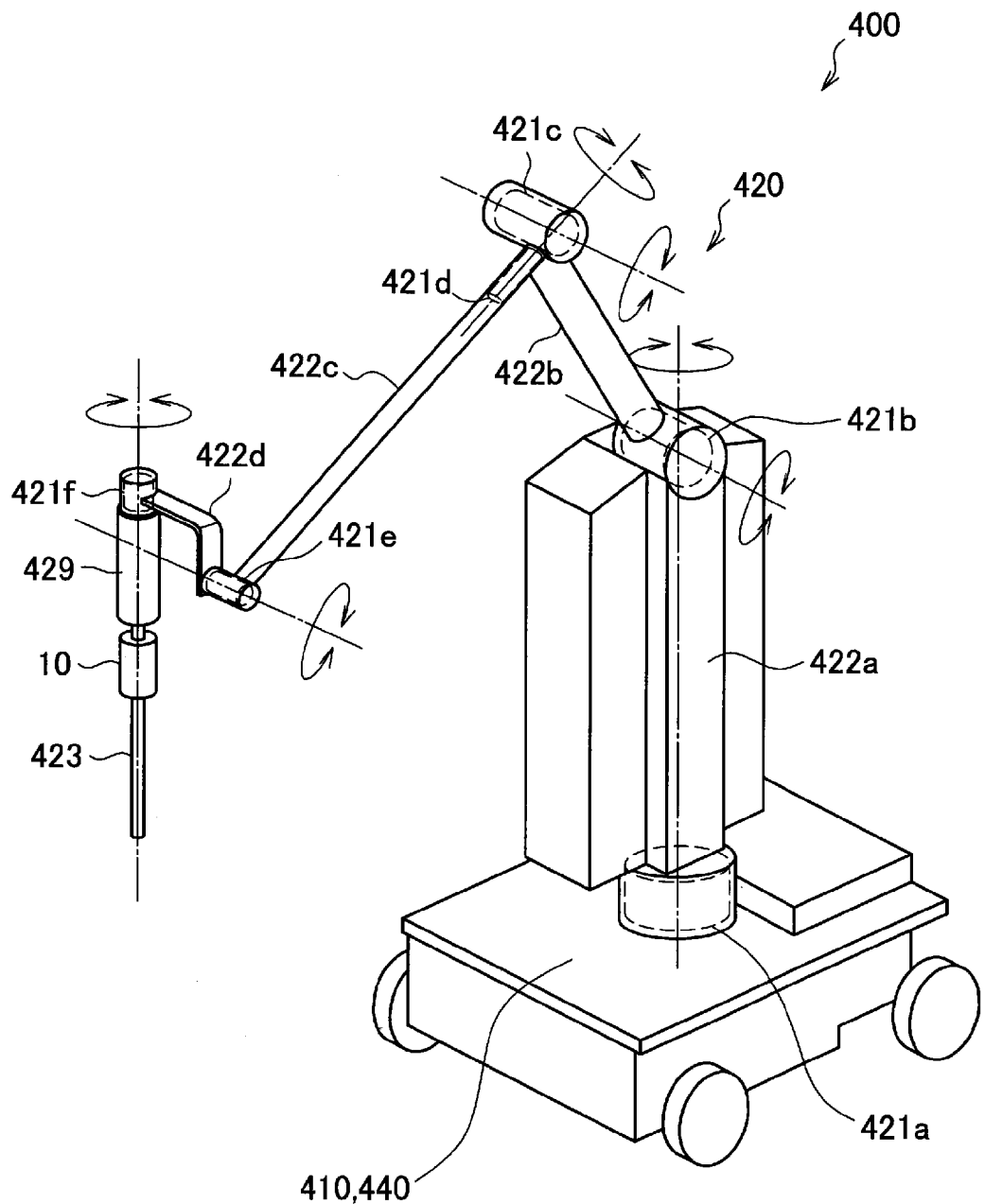

VIBRATION DETECTION MODULE, VIBRATION DETECTION METHOD, AND SURGICAL SYSTEM

CROSS REFERENCE TO RELATED APPLICATIONS

This application claims the benefit of Japanese Priority Patent Application JP 2015-105241 filed May 25, 2015 the entire contents of which are incorporated herein by reference.

TECHNICAL FIELD

The present disclosure relates to a medical apparatus, a medical apparatus vibration detection method and a surgical system.

BACKGROUND ART

In general, when surgery is performed, various medical instruments such as a forceps and an endoscope are inserted into a body cavity of a patient, and the medical instrument is manipulated from the outside of the body cavity by a surgeon. Technology in which a contact state of a distal end of the medical instrument with body tissues of the patient is detected and fed back to the surgeon in order to increase operability for the surgeon has been developed. For example, Patent Literatures 1 and 2 disclose technologies in which a sensor (a tactile sensor or a force sensor) configured to detect a contact state of the medical instrument with body tissues of the patient is provided at a distal end of the medical instrument inserted into the body cavity of the patient, and the contact state detected by the sensor is transmitted to the surgeon who manipulates the medical instrument as vibration.

CITATION LIST

Patent Literature

PTL 1: JP H10-94512A
PTL 2: JP H8-117228A

SUMMARY

Technical Problem

Here, as described above, in both technologies described in Patent Literatures 1 and 2, a sensor configured to detect a contact state is provided at a distal end of the medical instrument inserted into the body cavity of the patient. Of course, since the medical instrument should remain aseptic, it is necessary to provide a special structure for maintaining a degree of asepsis while a sensor is held when the sensor is attached to a distal end thereof. Therefore, there is concern about a structure of the medical instrument becoming complicated and cost increasing. In addition, since a configuration of the distal end of the medical instrument becomes large according to the provision of the sensor, there is concern about a load on the patient when the medical instrument is inserted into the body cavity increasing and accidental contact of the distal end of the medical instrument with body tissues in the body cavity increasing.

Here, the present disclosure proposes a medical apparatus, a medical apparatus vibration detection method and a surgical system which are novel and improved and through which it is possible to detect a contact state of a medical instrument with body tissues with a simpler configuration.

Solution to Problem

According to an embodiment of the present disclosure, there is provided a medical apparatus, including: medical vibration detection circuitry that is detachable from a medical instrument at an attachment position of the medical instrument in a longitudinal direction and that is configured to detect vibration generated in a distinct portion of the medical instrument, the distinct portion including at least a portion disposed toward a distal end of the medical instrument from the attachment position.

According to an embodiment of the present disclosure, there is provided a medical apparatus vibration detection method, including: attaching vibration detection circuitry that is detachable from a medical instrument at an attachment position of the medical instrument in a longitudinal direction, and detecting, by the vibration detection circuitry, vibration generated in a distinct portion of the medical instrument, the distinct portion including at least a portion of the medical instrument disposed toward a distal end of the medical instrument from the attachment position.

According to an embodiment of the present disclosure, there is provided a surgical system including: a medical instrument, a support arm device that supports the medical instrument, and medical vibration detection circuitry that is detachable from a medical instrument at an attachment position of the medical instrument in a longitudinal direction and that is configured to detect vibration generated in a distinct portion of the medical instrument, the distinct portion including at least a portion of the medical instrument disposed toward a distal end of the medical instrument from the attachment position.

Therefore, when sterilization treatment is performed, the vibration detection circuitry may be removed, and sterilization treatment may be separately performed on the medical instrument and the vibration detection circuitry. Accordingly, it is unnecessary to provide a special configuration in the medical instrument in consideration of sterilization treatment. In addition, since no vibration detection circuitry is attached to the distal end of the medical instrument that may actually approach or come into contact with body tissues of the patient, it is unnecessary to provide a special configuration for maintaining asepsis at the distal end of the medical instrument. Therefore, it is possible to further simplify a configuration of the medical instrument.

Advantageous Effects of Invention

According to the embodiment of the present disclosure described above, it is possible to detect a contact state of the medical instrument with body tissues with a simpler configuration. Note that the above effects are not necessarily limited, and any effect shown in this specification or other effects that may be understood from this specification may be achieved along with these effects or instead of these effects.

BRIEF DESCRIPTION OF DRAWINGS

FIG. 1 is a diagram illustrating a state in which a vibration detection module according to the present embodiment is attached to a forceps.

FIG. 2 is a perspective view illustrating an exterior of the vibration detection module according to the present embodiment.

FIG. 3 is an exploded perspective view illustrating the vibration detection module according to the present embodiment.

FIG. 4 is a perspective view illustrating a state of a cross section when the vibration detection module according to the present embodiment is cut in an insertion direction of a forceps.

FIG. 5 is a block diagram illustrating one configuration example of a surgical system to which the vibration detection module according to the present embodiment may be applied.

FIG. 6 is a diagram illustrating one configuration example of a support arm device that may configure a slave of a surgical system according to the present embodiment.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will proceed in the following order.
1. Configuration of vibration detection module
2. Configuration of surgical system
3. Configuration example of support arm device
4. Modification examples
4-1. Use of vibration detection module for damping control
4-2. Other application examples of vibration detection module
4-3. Use of detection values of other vibration sensors
4-4. Use of directional vibration sensor
4-5. Number of vibration sensors mounted on vibration detection module
4-6. Use of information about actuator control
4-7. Other methods of presenting vibration
5. Supplement 1. Configuration of Vibration Detection Module A configuration of a vibration detection module according to one embodiment of the present disclosure will be described with reference to FIGS. 1 to 4. FIG. 1 is a diagram illustrating a state in which the vibration detection module according to the present embodiment is attached to a forceps. FIG. 2 is a perspective view illustrating an exterior of the vibration detection module according to the present embodiment. FIG. 3 is an exploded perspective view illustrating the vibration detection module according to the present embodiment. FIG. 4 is a perspective view illustrating a state of a cross section when the vibration detection module according to the present embodiment is cut in an insertion direction of a forceps. Note that, in FIG. 4, in order to show a positional relation between the vibration detection module according to the present embodiment and a forceps, the forceps is also shown.

As illustrated in FIG. 1, a state in which a vibration detection module 10 according to the present embodiment is attached to a forceps 301, which is an exemplary medical instrument used for a patient when surgery is performed, is illustrated. In this manner, the vibration detection module 10 according to the present embodiment is attached to a medical instrument when used and detects vibration generated in the medical instrument.

As illustrated in FIG. 1, the forceps 301 is supported by an arm portion 303 of a support arm device capable of supporting various medical instruments, and a position and an orientation of the forceps 301 are controlled by the arm portion 303.

In the present embodiment, the arm portion 303 is operated by a so-called master and slave method. That is, the arm portion 303 may be controlled remotely by a surgeon through an input device such as a controller that is installed separately from the arm portion 303 and the forceps 301.

The forceps 301 is a long tubular instrument having a distal end at which an end effector is provided. When surgery is performed, an area having a predetermined length including the distal end is inserted into a body cavity of the patient. The end effector includes a pair of openable blades. It is possible to grip or cut body tissues of the patient or grip a needle when body tissues are sutured by the blades.

In the present embodiment, the forceps 301 is a so-called robot forceps that is operated by the master and slave method. For example, the forceps 301 may be controlled remotely together with the arm portion 303 by the surgeon through the above-described input device configured to control the arm portion 303 remotely. Although not illustrated for simplicity of illustration, one or a plurality of joint portions for changing a position and an orientation of the end effector may be provided in the forceps 301. The surgeon can perform manipulation through the input device, operate each of the joint portions to adjust the position and the orientation of the end effector, and perform an opening and closing operation of the end effector.

In this manner, in the present embodiment, the vibration detection module 10 is applied to the surgical system of a so-called master and slave method. In the surgical system of the master and slave method, various medical instruments or an observation unit (for example, a microscope or an endoscope) for observing an operative portion are supported by the plurality of arm portions, and the plurality of arm portions and medical instruments are controlled by the surgeon remotely through the input device such as a controller installed separately from the plurality of arm portions, and thus surgery is performed. The vibration detection module 10 according to the present embodiment may be attached to one or a plurality of various medical instruments. Note that the surgical system of the master and slave method will be described again in the following (2. Configuration of surgical system).

Note that surgery to be assumed in the present embodiment may be both open surgery and endoscopic surgery. For example, in the open surgery, an operative portion is imaged by a so-called video microscope capable of electronically imaging the operative portion. In addition, in the endoscopic surgery, an endoscope is inserted into the body cavity of the patient together with the forceps 301, and the operative portion is imaged by the endoscope. An image of the operative portion imaged by the observation unit such as a video microscope or an endoscope is displayed on a display device that is arranged at a position that the surgeon can confirm by sight. The surgeon performs surgery while observing a state of the operative portion according to the image projected on the display device. Also, the display device may be installed in an operating room or mounted on a device that is worn by the surgeon when used such as a wearable device of a head mounted display (HMD) or eyeglass type.

In FIG. 1, in the configuration of the surgical system of the master and slave method in this manner, only the arm portion 303 and the forceps 301 supported by the one arm portion 303 are illustrated as an example. Hereinafter, as an example, as illustrated in FIG. 1, a case in which the vibration detection module 10 according to the present embodiment is attached to the forceps 301 will be exemplified, and a configuration and a function of the vibration detection module 10 will be described.

The vibration detection module 10 is attached to a proximal end side (that is, a side connected to the arm portion 303) of the forceps 301 and detects vibration generated in the forceps 301 at a distal end side relative to the attachment position of the vibration detection module 10, that is, at a portion that approaches or comes into contact with body tissues of the patient. For example, the vibration detection module 10 can detect vibration generated in the forceps 301 when the forceps 301 inserted into the body cavity of the patient comes into contact with body tissues in the body cavity. In this manner, according to the present embodiment, a contact state of the forceps 301 in the body cavity and body tissues may be detected by the vibration detection module 10 installed outside the body cavity.

Here, in the following description, for convenience of description, in the forceps 301, a portion serving as a vibration detection target of the vibration detection module 10 is referred to as a "distal end side." However, as described above, since the vibration detection module 10 detects vibration generated in the forceps 301 at a distal end side relative to the attachment position of the vibration detection module 10, the vibration detection module 10 may detect not only vibration generated in a portion near a distal end of the forceps 301 but also vibration generated in a middle portion (a portion between the attachment position of the vibration detection module 10 and the distal end of the forceps 301) of the forceps 301. Therefore, the term "distal end side" does not necessarily indicate only a portion near the distal end of the forceps 301 but indicates the entire portion that includes the distal end and the middle portion and serves as the vibration detection target of the vibration detection module 10.

Note that, in the example illustrated in FIG. 1, while the vibration detection module 10 is attached to the forceps 301, the present embodiment is not limited thereto. In the present embodiment, an instrument serving as a vibration detection target may be a long medical instrument and a type thereof is not limited. The vibration detection module 10 may be attached to various long medical instruments. In the present embodiment, the vibration detection module 10 is attached to a portion of the long medical instrument in a longitudinal direction, and may detect vibration generated in another portion of the medical instrument separated from the attachment position in the longitudinal direction.

A configuration of the vibration detection module 10 will be described in further detail. As illustrated in FIGS. 2 to 4, the vibration detection module 10 mainly includes a housing 110 and a first vibration sensor 120 and a second vibration sensor 130 disposed in the housing 110.

The housing 110 has substantially a hollow cylindrical shape and apertures are provided at substantially a center of a top and a bottom of the cylindrical shape. When the vibration detection module 10 is attached to the forceps 301, the forceps 301 is inserted into two apertures of the housing 110.

The housing 110 includes two members 111 and 112 (the first member 111 and the second member 112) that are divided in a plane that passes through the two apertures. Therefore, when the first member 111 and the second member 112 are assembled with the forceps 301 interposed therebetween, the housing 110 (that is, the vibration detection module 10) is attached to the forceps 301 (refer to FIG. 4).

In this manner, the vibration detection module 10 is detachable from the forceps 301. In this case, the vibration detection module 10 may be attachable to the existing forceps 301. Accordingly, it is unnecessary to provide a special configuration for attaching the vibration detection module 10 to the forceps 301, and the existing forceps 301 can be used without change.

In addition, it is preferable that the vibration detection module 10 be attachable to the forceps 301 using a simple method without using a tool, for example, a method in which engaging members provided in the first member 111 and the second member 112 are engaged to each other to be connected together. Accordingly, it is possible to increase workability when the vibration detection module 10 is attached to the forceps 301.

A material of the housing 110 is not particularly limited. In view of maintaining asepsis of the vibration detection module 10 when surgery is performed, the housing 110 is preferably made of an antibacterial material and/or a material that can withstand sterilization treatment. In addition, in order to suppress vibration (for example, conversation or music to be described below) that may become noise in an external environment from being transmitted to the first vibration sensor 120 and the second vibration sensor 130 disposed in the housing 110, the housing 110 is preferably made of a material having a relatively high specific gravity.

A sealing member 140 configured to seal the housing 110 when the housing 110 is attached to the forceps 301 is provided in a contact portion (that is, an edge in a divided surface of the housing 110) between the first member 111 and the second member 112 and a contact portion (that is, an edge of the aperture) with the forceps 301 in the aperture of the housing 110. By providing the sealing member 140, when the housing 110 is attached to the forceps 301, sealability in the housing 110 is maintained, and it is possible to block the first vibration sensor 120 and the second vibration sensor 130 provided in the housing 110 from the external environment.

For example, during surgery, the surgeon and other medical staff converse, and music is played in order to relieve tension of the surgeon. Such conversation or music may serve as noise to vibration that is normally intended to be detected by the first vibration sensor 120 and the second vibration sensor 130 and generated in the forceps 301. When sealability in the housing 110 is maintained by the sealing member 140, it is possible to reduce noise caused by the external environment that may be detected in the first vibration sensor 120 and the second vibration sensor 130.

For example, the sealing member 140 is made of a soft material such as rubber. However, the present embodiment is not limited thereto, and various known members that may be generally used to seal a hollow member can be used as the sealing member 140. In addition, a portion in which the sealing member 140 is disposed is not limited to the above-described portion. For example, when there is a gap that spatially connects an inside and an outside of the housing 110 in a portion other than the contact portion between the first member 111 and the second member 112 or the aperture for inserting the forceps 301, the sealing member 140 may be appropriately disposed to close such a gap.

In addition, in the examples illustrated in FIGS. 1 to 4, while the sealing member 140 is configured as a separate member from the housing 110, the present embodiment is not limited thereto. For example, according to two-color molding, any of the first member 111 and the second member 112 of the housing 110 and the sealing member 140 may be formed as an integral member. Accordingly, the housing 110 is more reliably sealed, and an effect of blocking the first vibration sensor 120 and the second vibration sensor 130 from the external environment can be further obtained.

The first vibration sensor 120 is an auditory sensor configured to detect vibration (hereinafter referred to as "auditory vibration" for convenience of description) of a frequency band corresponding to an auditory sense of a human. For example, the first vibration sensor 120 detects vibration of a frequency band corresponding to an audible range (for example, about 20 Hz to about 20 kHz) of a human. The first vibration sensor 120 is, for example, a microphone, and is arranged in the housing 110 such that a sound collection unit of the first vibration sensor 120 comes into contact with the forceps 301 when the housing 110 is attached to the forceps 301. The first vibration sensor 120 can detect sound (for example, sound when the end effector of the forceps 301 grips body tissues of the patient) that has been generated in a distal end side of the forceps 301 and then transmitted into the forceps 301.

In the exemplified drawing, the first vibration sensor 120 is arranged in the first member 111. Although not illustrated, a support member for supporting the first vibration sensor 120 is appropriately provided in the first member 111. The first vibration sensor 120 is fixedly supported in the first member 111 by the support member.

The second vibration sensor 130 is a tactile sensor configured to detect vibration (hereinafter referred to as "tactile vibration" for convenience of description) of a frequency band corresponding to a tactile sense of a human. For example, the second vibration sensor 130 detects vibration of a frequency corresponding to a frequency band (for example, several Hz to about 1 kHz) detectable by human skin. The second vibration sensor 130 is a multi-axis acceleration sensor having, for example, 3 or more axes. The second vibration sensor 130 is fixedly disposed with respect to the housing 110. Tactile vibration (for example, tactile vibration generated when the end effector of the forceps 301 grips body tissues of the patient) that has been generated in the distal end side of the forceps 301 and then transmitted through the forceps 301 may be detected by the second vibration sensor 130 through the housing 110.

In the exemplified drawing, the second vibration sensor 130 is arranged in the second member 112. Although not illustrated, a support member for supporting the second vibration sensor 130 is appropriately provided in the second member 112. The second vibration sensor 130 is fixedly supported in the second member 112 by the support member.

A signal indicating auditory vibration detected by the first vibration sensor 120 and a signal indicating tactile vibration detected by the second vibration sensor 130 are transmitted to a circuit board configured to perform various types of signal processing such as amplification and filtering on such signals using a cable 150. The signal that underwent various types of signal processing in the circuit board is transmitted to a vibration presentation unit (not illustrated) in a hand of the surgeon who manipulates the forceps 301 and the arm portion 303. Auditory vibration detected by the first vibration sensor 120 and tactile vibration detected by the second vibration sensor 130 are transmitted to the surgeon by the vibration presentation unit.

Also, the cable 150 may extend to the outside of the housing 110 through the aperture provided in the housing 110. However, similarly to the aperture into which the above-described forceps 301 is inserted, the aperture into which the cable 150 is inserted may also be sealed by the sealing member 140. In addition, the signal indicating auditory vibration detected by the first vibration sensor 120 and the signal indicating tactile vibration detected by the second vibration sensor 130 may not necessarily be transmitted by the cable 150, but may be wirelessly transmitted to the circuit board according to various known communication methods.

The vibration presentation unit includes, for example, a speaker or a vibration element. Auditory vibration (that is, sound) detected by the first vibration sensor 120 is transmitted to the surgeon by the speaker of the vibration presentation unit. In addition, tactile vibration detected by the second vibration sensor 130 is transmitted to the surgeon by the vibration element of the vibration presentation unit. In this manner, when auditory vibration and tactile vibration generated in the distal end side of the forceps 301 are transmitted to the surgeon, the surgeon can more intuitively feel a contact state of the forceps 301 with body tissues of the patient while manipulating the forceps 301. Also, a method of transmitting auditory vibration and tactile vibration to the surgeon through the vibration presentation unit in this manner will be described again in the following (2. Configuration of surgical system).

Here, tactile vibration that may be detected by the second vibration sensor 130 when the forceps 301 comes into contact with body tissues of the patient may include body tissue surface texture information, and/or body tissue rigidity information. For example, based on the transmitted tactile vibration, the surgeon can intuitively recognize a state (such as smooth or rough) of a surface of body tissues with which the forceps 301 is currently in contact or elasticity (such as soft or hard) of body tissues with which the forceps 301 is currently in contact. For example, in the same body tissues, when a lesioned part and a normal part have a significantly different surface state or rigidity, such body tissue surface texture information and/or rigidity information may help in confirmation of the lesioned part. For example, a use method in which the forceps 301 is moved to trace a surface of body tissues, tactile vibration along the way is detected and transmitted to the surgeon, and surface texture information and/or rigidity information may be actively obtained may be assumed.

In addition, auditory vibration that may be detected by the first vibration sensor 120, that is, sound generated from body tissues, may be information that is beneficial for determining whether the body tissues are in a normal state. For example, when a blood vessel is sutured, an examination method in which sound waves are used to confirm whether blood flows normally in the sutured blood vessel is used. In the present embodiment, in various types of examinations using such sound waves, auditory vibration detected by the first vibration sensor 120 may be used.

In this manner, when auditory vibration and tactile vibration are transmitted to the surgeon, the surgeon can obtain a greater amount of information about body tissues in contact with the distal end side of the forceps 301.

Here, although not illustrated, the force sensor may be provided in a portion connecting the arm portion 303 and the forceps 301. In addition, a force sensor (a torque sensor) configured to detect a force applied to each of the joint portions may be provided in the joint portions of the arm portion 303. In the present embodiment, a force applied to the forceps 301 may be detected by such a force sensor, and transmitted to the surgeon who manipulates the forceps 301. In this case, the force applied to the forceps 301 detected by the force sensor, and auditory vibration and tactile vibration generated in the distal end side of the forceps 301 are detected by the vibration detection module 10 and transmitted together to the surgeon. Also, the force sensor provided in the portion connecting the arm portion 303 and the forceps 301 may be a force sensor that is provided separately in order to detect the force applied to the forceps 301 or a torque sensor provided in the joint portion when the joint portion is arranged in the portion connecting the arm portion 303 and the forceps 301.

The surgeon may also recognize the contact state of the forceps 301 with body tissues according to feedback of a force by the force sensor. However, in general, the force sensor includes, for example, a strain gauge or a pressure sensitive element, and when a magnitude or a direction of a force is changed at a relatively high frequency (for example, several Hz or more), it is difficult to accurately detect a vibrating force thereof in many cases. Therefore, it can be considered hard to say that feedback to the surgeon from the force applied to the forceps 301 detected by the force sensor is enough to transmit sufficient information indicating the contact state of the forceps 301 with body tissues to the surgeon.

It can be understood that the first vibration sensor 120 and the second vibration sensor 130 in the present embodiment are used to detect vibration of a frequency band that is difficult to detect by such a force sensor. That is, according to the present embodiment, when vibration detected by the first vibration sensor 120 and the second vibration sensor 130 is fed back to the surgeon, it is possible to transmit vibration of a wider frequency band that is not possible to obtain when only feedback of a force by the force sensor is provided to the surgeon. Therefore, since it is possible to transmit a greater amount of information indicating the contact state of the forceps 301 with body tissues to the surgeon, the surgeon can feel the contact state more intuitively and more realistically.

Here, for simplicity of description, auditory vibration detected by the first vibration sensor 120 and tactile vibration detected by the second vibration sensor 130 will be simply referred to in general as "vibration detected by the first vibration sensor 120 and the second vibration sensor 130" below. However, in view of the above, in this specification, "vibration" detected by the first vibration sensor 120 and the second vibration sensor 130 (that is, "vibration" that may be detected by the vibration detection module 10) refers to vibration of a frequency band that is generally difficult to detect by the force sensor, unless otherwise described.

The configuration of the vibration detection module 10 according to the present embodiment has been described above with reference to FIGS. 1 to 4.

Here, in existing configurations exemplified in Patent Literatures 1 and 2, a sensor configured to detect a contact state of a medical instrument such as the forceps with body tissues of the patient is provided integrally with the medical instrument at a distal end of the medical instrument. Therefore, there are concerns of a configuration of the distal end of the medical instrument becoming large, a load on the patient when the medical instrument is inserted into the body cavity increasing, and accidental contact of the distal end of the medical instrument with body tissues in the body cavity increasing.

In addition, while sterilization treatment is performed on the medical instrument before and after surgery, an autoclave is generally used for the sterilization treatment. Since the medical instrument is exposed to a high temperature and high pressure liquid in the autoclave, when a sensor and a medical instrument are integrally configured as in the configurations described in Patent Literatures 1 and 2, it is necessary for the sensor to have a configuration that withstands an environment of the autoclave. Therefore, in the configurations described in Patent Literatures 1 and 2, it is necessary to set a configuration of a portion in which the sensor is arranged as a special configuration that protects the sensor from the high temperature and high pressure liquid and set the sensor itself as a special sensor that withstands an environment of the autoclave, which causes concerns about cost increasing. Alternatively, in sterilization treatment for the medical instrument in which the sensor is provided, use of a method other than the autoclave can also be considered in order not to damage the sensor. However, in this case, since a medical staff is forced to perform a new task, there is concern of a task of a medical staff who performs surgery preparation or cleanup becoming complicated.

In addition, in the configurations described in Patent Literatures 1 and 2, the sensor is provided at the distal end of the medical instrument, and a circuit board configured to perform various types of signal processing on a signal indicating a detection value of the sensor is installed outside the body cavity. Therefore, it is necessary to provide a wire for transmitting the signal indicating a detection value of the sensor to the circuit board along the medical instrument. Accordingly, for example, a catheter having a dedicated structure for the wire is prepared separately, which may cause an increase in additional costs. In addition, as described above, since the signal indicating a detection value of the sensor is transmitted a relatively long distance to the circuit board outside the body cavity through the wire, there is concern of noise being superimposed along the way and an S/N ratio of a signal deteriorating.

In addition, in the configurations described in Patent Literatures 1 and 2, the pressure sensitive element is used as the sensor. In general, the pressure sensitive element has a limited resolution and has difficulty detecting a vibrating force at a high frequency or a relatively low force. Therefore, it is hard to say that the pressure sensitive element is appropriate to detect the contact state of the medical instrument with body tissues.

On the other hand, as described above, the vibration detection module 10 according to the present embodiment is detachable from the proximal end side of the forceps 301, and detects vibration generated in the distal end side of the forceps 301 while attached to the proximal end side. Therefore, it is possible to implement the distal end of the forceps 301 with a simpler and smaller configuration, and reduce a load on the patient or a risk of unintended contact with body tissues described above.

In addition, in this case, since the vibration detection module 10 may be attachable to the existing forceps 301, it is unnecessary to provide a special configuration for attaching the vibration detection module 10 to the forceps 301. Therefore, an existing forceps can be used without change as the forceps 301, which does not lead to a significant increase in costs.

In this manner, according to the present embodiment, it is possible to detect vibration generated in the medical instrument with a simpler configuration.

In addition, since the vibration detection module 10 is detachable from the forceps 301, the vibration detection module 10 is attached to the forceps 301 only as necessary, and the vibration detection module 10 can be removed from the forceps 301 in a preparation or cleanup step. Therefore, since processes of the related art can be applied without change as processes performed on the forceps 301 when preparation or cleanup is performed, a preparation or cleanup task does not become complicated, and it is possible to further increase convenience for the medical staff related to the task.

For example, in sterilization treatment, the vibration detection module 10 is removed from the forceps 301, and the sterilization treatment can be separately performed on the vibration detection module 10 and the forceps 301. Therefore, the sterilization treatment can be performed on the forceps 301 using a known method, for example, the autoclave, and a task of the medical staff does not become complicated. In addition, for the vibration detection module 10, a sterilization treatment method that is less likely to influence operations of the first vibration sensor 120 and the second vibration sensor 130 can be used, for example, sterilization treatment using plasma. In this manner, in the present embodiment, since the vibration detection module 10 is detachable from the forceps 301, sterilization treatment can be performed on the vibration detection module 10 and the forceps 301 using an appropriate method.

Also, the vibration detection module 10 may not be assumed to be repeatedly used, but may be assumed to be disposable. In this case, sterilization treatment is necessary in advance before surgery, but it is unnecessary to perform sterilization treatment on the vibration detection module 10 after surgery in medical facilities such as hospitals. Therefore, it is possible to decrease a load of the sterilization treatment task of the vibration detection module 10 in medical facilities. Alternatively, the vibration detection module 10 may be covered with a drape when surgery is performed. In this case, since it is unnecessary to perform special sterilization treatment on the vibration detection module 10 itself, it is possible to further decrease a load of the sterilization treatment task.

In addition, in the present embodiment, since vibration of the distal end side of the forceps 301 is detected by the vibration detection module 10 attached to the proximal end side of the forceps 301, the circuit board configured to perform various types of signal processing on a signal indicating a detection value of the vibration detection module 10 can be installed relatively close to the vibration detection module 10. Therefore, a wire connecting the vibration detection module 10 and the circuit board can be shorter and it is possible to suppress noise to the signal in the wire from being superimposed.

In addition, the vibration detection module 10 includes the first vibration sensor 120 configured to detect auditory vibration and the second vibration sensor 130 configured to detect tactile vibration. Therefore, according to the vibration detection module 10, it is possible to detect vibration of a frequency band that is difficult to detect using a general force sensor, and it is possible to detect a more detailed contact state of the medical instrument with body tissues. In addition, when the detected auditory vibration and tactile vibration are transmitted to the surgeon, the surgeon can obtain a more detailed contact state of the forceps 301 with body tissues of the patient, which was not possible to obtain with feedback by the general force sensor. Also, the vibration detection module 10 may not necessarily be configured to detect both auditory vibration and tactile vibration, but may be configured to detect at least one of auditory vibration and tactile vibration (that is, to include at least one of the first vibration sensor 120 and the second vibration sensor 130). When at least one of auditory vibration and tactile vibration is detectable, it is possible to detect vibration of a frequency band that is difficult to detect using the general force sensor, and it is possible to transmit a more detailed contact state to the surgeon.

For example, when auditory vibration and tactile vibration are transmitted to the surgeon, the surgeon can more realistically feel, for example, a sense of gripping body tissues using the forceps 301 or a sense of sticking a needle into body tissues when a suture procedure is performed on body tissues while the needle is held using the forceps 301. Therefore, workability for the surgeon increases. In addition, for example, when the forceps 301 unintentionally comes into contact with vulnerable tissues such as soft tissues, the surgeon can recognize the contact more intuitively and can take an appropriate action immediately, for example, moving the forceps 301. Therefore, it is possible to increase safety when surgery is performed.

2. Configuration of Surgical System

The configuration of the surgical system to which the vibration detection module 10 according to the present embodiment described above may be applied will be described with reference to FIG. 5. FIG. 5 is a block diagram illustrating one configuration example of a surgical system to which the vibration detection module 10 according to the present embodiment may be applied.

FIG. 5 illustrates a configuration of a surgical system of a so-called master and slave method as the surgical system according to the present embodiment. In the surgical system of the master and slave method, according to an instruction input by the surgeon on a master side through the input device such as a controller, an arm portion on a slave side and a medical instrument attached to the arm portion are driven, and various types of treatment are performed on an operative portion of the patient by the medical instrument.

As illustrated in FIG. 5, a surgical system 1 according to the present embodiment includes a support arm device 210 having an arm portion that includes a distal end to which a medical instrument such as a forceps is attached, an input device 220 configured to manipulate the support arm device 210, a control system 230 configured to drive the support arm device 210 according to an instruction input through the input device 220, and a vibration transmission unit 240 configured to transmit vibration detected by the vibration detection module 10 attached to the support arm device 210 to the input device 220. The support arm device 210 corresponds to a slave and the input device 220 corresponds to a master.

Note that, in the block diagram illustrated in FIG. 5, only components that are particularly necessary to describe an embodiment of the present disclosure are illustrated. The surgical system 1 may include various components of a general surgical system of a master and slave method other than the illustrated components. Since various known components are applied as components (not illustrated), details thereof will be omitted.

In the surgical system 1, an information transmission system may be broadly classified as a drive control system of the support arm device 210 and a system of transmitting vibration detected by the vibration detection module 10 to the surgeon. First, the drive control system of the support arm device 210 will be described.

In drive control of the support arm device 210, information indicating an instruction for driving an arm portion of the support arm device 210 input by the surgeon through an input unit 221 of the input device 220 is transmitted to the control system 230. As the robot forceps described above, when the medical instrument includes a drive portion, information indicating an instruction for driving the medical instrument may also be input to the control system 230 from the input unit 221 of the input device 220.

The input unit 221 may include an input mechanism, for example, a lever, a grip and/or a button. A specific configuration of the input unit 221 is not limited thereto. Various known components that may be provided in the input device of the general surgical system of the master and slave method may be applied as the input unit 221.

The control system 230 performs various types of calculation related to drive control of the support arm device 210. For example, in the control system 230, based on an instruction input through the input unit 221, a control amount for driving the arm portion of the support arm device 210 is computed. The arm portion may be configured by rotatably connecting a plurality of links to each other by the joint portion. For example, when drive control of the support arm device 210 is performed by force control, as a control amount thereof, a torque that has to be generated in joint portions in order for the arm portion to implement a desired operation instructed by the surgeon may be computed. Alternatively, when drive control of the support arm device 210 is performed by position control, as a control amount thereof, a rotation angle that has to be generated in joint portions in order for the arm portion to implement a desired operation instructed by the surgeon may be computed. In addition, when the medical instrument includes the drive portion, similarly, a control amount for driving the medical instrument may be calculated by the control system 230.

In the present embodiment, as a method of drive control of the support arm device 210 (the arm portion and/or the medical instrument), various known control methods may be used. As the control system 230, a system compatible with an employed control method may be appropriately constructed. Since a specific configuration of the control system 230 may be similar to an existing configuration according to various control methods, details thereof will be omitted.

Information about the control amount computed by the control system 230 is transmitted to a drive unit 211 of the support arm device 210. The drive unit 211 corresponds to, for example, a motor that is provided in joint portions of the arm portion and configured to rotatably drive the joint portions. When the motor is driven according to the control amount computed by the control system 230, the arm portion is operated according to an instruction by the surgeon through the input device 220. In addition, when the medical instrument includes the drive portion, the drive unit 211 may correspond to a motor configured to operate the drive portion. When the motor is driven according to the control amount computed by the control system 230, the medical instrument is operated according to an instruction by the surgeon through the input device 220.

In addition, the support arm device 210 includes a state detection unit 212 configured to detect a state of the arm portion. The state detection unit 212 corresponds to, for example, a force sensor (a torque sensor) or an encoder provided in joint portions of the arm portion. A force (torque) applied to each of the joint portions may be detected by the force sensor. In addition, a rotation angle of each of the joint portions may be detected by the encoder. Information indicating a state of the arm portion detected by the state detection unit 212 is transmitted to the control system 230. The control system 230 sequentially recognizes a current state of the arm portion based on the information, and computes the above-described control amount based on the recognized current state of the arm portion.

Here, the force applied to the joint portions detected by the force sensor may reflect the force applied to the medical instrument attached to the distal end of the arm portion. In the surgical system 1, by the control system 230, a force component applied to the medical instrument is extracted from the force applied to the joint portions detected by the force sensor and transmitted to a power presentation unit 222 of the input device 220. The power presentation unit 222 includes, for example, a servomotor. When a lever or the like of the input unit 221 is driven such that, for example, a resistance with respect to a manipulation of the input unit 221 by the surgeon is provided according to the force applied to the medical instrument, the force applied to the medical instrument is presented to the surgeon. In this manner, the surgical system 1 includes functions of detecting a force applied to the medical instrument and feeding the force back to the surgeon.

Next, a system of transmitting vibration detected by the vibration detection module 10 will be described. In the surgical system 1, in the support arm device 210, the vibration detection module 10 is attached to the proximal end side of the medical instrument. As described above in (1. Configuration of vibration detection module), the first vibration sensor 120 and the second vibration sensor 130 are mounted on the vibration detection module 10. Auditory vibration and tactile vibration generated in the medical instrument are detected by these vibration sensors.

The first vibration sensor 120 is, for example, a condenser microphone, and detects auditory vibration (that is, sound) generated in the forceps. The second vibration sensor 130 is, for example, an acceleration sensor, and detects tactile vibration generated in the forceps. A signal indicating vibration detected by the first vibration sensor 120 and the second vibration sensor 130 is transmitted to a vibration presentation unit 223 of the input device 220 through the vibration transmission unit 240.

Specifically, the vibration transmission unit 240 performs various types of signal processing such as an amplification process and a filtering process on the signal indicating vibration detected by the vibration detection module 10, and transmits the processed signal to the vibration presentation unit 223. For example, the vibration transmission unit 240 includes an amplifier configured to appropriately amplify a signal or a filter configured to extract only a component of a significant frequency band from the detected vibration.

In addition, the vibration presentation unit 223 of the input device 220 includes various devices configured to present vibration detected by the vibration detection module 10 to the surgeon. In the present embodiment, the vibration presentation unit 223 includes an auditory vibration presentation unit 224 including an audio output device, for example, a speaker or an earphone, and a tactile vibration presentation unit 225 including a vibration element, for example, a voice coil.

In the exemplified drawing, the vibration transmission unit 240 includes pre-AMPs 241 and 244, low pass filters 242 and 245 (LPFs 242 and 245), and main AMPs 243 and 246. The signal indicating auditory vibration detected by the first vibration sensor 120 is amplified by the pre-AMP 241, only a frequency component of a low frequency band is extracted by the LPF 242, and a frequency component of the low frequency band is amplified by the main AMP 243 and is transmitted to the auditory vibration presentation unit 224 of the input device 220. When audio corresponding to a signal indicating auditory vibration that has been processed by the pre-AMP 241, the LPF 242 and the main AMP 243 is output from the speaker of the auditory vibration presentation unit 224, auditory vibration generated in the medical instrument is transmitted to the surgeon.

In addition, the signal indicating tactile vibration detected by the second vibration sensor 130 is amplified by the pre-AMP 244, only a frequency component of a low frequency band is extracted by the LPF 245, and the frequency component of the low frequency band is amplified by the main AMP 246 and transmitted to the tactile vibration presentation unit 225 of the input device 220. When the voice coil of the tactile vibration presentation unit 225 vibrates according to a signal indicating tactile vibration that has been processed by the pre-AMP 244, the LPF 245 and the main AMP 246, tactile vibration generated in the medical instrument is transmitted to the surgeon.

When only a significant frequency component is extracted by the LPFs 242 and 245, noise is reduced, and only a component considered to be more beneficial for the surgeon within the detected vibration may be transmitted to the surgeon. In addition, when the frequency component extracted by the LPFs 242 and 245 is amplified by the main AMPs 243 and 246, the component considered to be more beneficial for the surgeon may be emphasized and transmitted to the surgeon. In this manner, when signal processing is appropriately performed by the vibration transmission unit 240, more distinct vibration in which noise is reduced is presented to the surgeon.

Note that the pre-AMPs 241 and 244 may not be provided as a member separated from the vibration detection module 10 as one function of the vibration transmission unit 240 but may be provided in the vibration detection module 10. Accordingly, it is possible to further reduce noise that may be superimposed in the signal while the signal indicating vibration detected by the vibration detection module 10 is transmitted to the vibration transmission unit 240.

In addition, the configuration of the vibration transmission unit 240 is not limited to the illustrated example. The vibration transmission unit 240 may be appropriately configured such that a desired frequency component may be further emphasized from the vibration detected by the vibration sensor according to a characteristic of the vibration sensor provided in the vibration detection module 10. For example, when a frequency band that should be further emphasized and transmitted to the surgeon such as a frequency band indicating abnormality of body tissues with which the medical instrument approaches or comes into contact is known in advance, the vibration transmission unit 240 may be configured such that a component of the frequency band may be further emphasized. In addition, in the vibration transmission unit 240, other than the amplification process and the filtering process described above, various types of processing that are generally performed as signal processing on a signal indicating vibration may be performed. As the configuration of the vibration transmission unit 240, various known configurations may be applied to implement such functions.

In addition, the configuration of the vibration presentation unit 223 is not limited to the above-described configuration. The vibration presentation unit 223 may be appropriately configured such that auditory vibration and tactile vibration may be appropriately transmitted to the surgeon. As the configuration of the vibration presentation unit 223, various known configurations used when vibration is presented to a human may be applied. Note that other configuration examples of the vibration presentation unit 223 will be described again in the following (4-7. Other methods of presenting vibration).

The configuration of the surgical system 1 to which the vibration detection module 10 according to the present embodiment may be applied has been described above with reference to FIG. 5.

3. Configuration Example of Support Arm Device

One configuration example of a support arm device that may constitute a slave of the surgical system 1 illustrated in FIG. 5 will be described with reference to FIG. 6. FIG. 6 is a diagram illustrating one configuration example of a support arm device that may constitute a slave of the surgical system 1 according to the present embodiment.

As illustrated in FIG. 6, a support arm device 400 includes a base portion 410, an arm portion 420 and a control device 440. The support arm device 400 corresponds to the above-described support arm device 210 illustrated in FIG. 5 and is a medical support arm device configured to support a medical instrument such as a forceps when surgery is performed.

The base portion 410 is a base table of the support arm device 400, and the base portion 410 extends from the arm portion 420. Casters are provided at the base portion 410. The support arm device 400 comes into contact with a floor through the casters, and is movable on the floor by the casters. However, the configuration of the support arm device 400 according to the present embodiment is not limited thereto. For example, the support arm device 400 may be configured such that the arm portion 420 is directly attached to a ceiling or a wall surface of the operating room without the base portion 410. For example, when the arm portion 420 is attached to the ceiling, the support arm device 400 is configured such that the arm portion 420 is suspended from the ceiling.

The control device 440 configured to perform various types of information processing in the surgical system 1 illustrated in FIG. 5 is provided in the base portion 410. The control device 440 may be a processor, for example, a central processing unit (CPU) or a digital signal processor (DSP). Alternatively, the control device 440 may be a control board or a microcomputer on which such a processor and a storage element such as a memory are mounted. When the processor of the control device 440 performs various types of signal processing according to a predetermined program, various operations in the surgical system 1 are performed.

Specifically, the control device 440 performs various types of processing performed by the control system 230 illustrated in FIG. 5 and integrally controls operations of the support arm device 400. In addition, the control device 440 performs various types of processing performed by the vibration transmission unit 240 illustrated in FIG. 5, performs various types of processing such as amplification and filtering on the signal indicating vibration detected by the vibration detection module 10, and transmits the signal to an input device (not illustrated) in a hand of the surgeon.

The arm portion 420 includes a plurality of joint portions 421*a*, 421*b*, 421*c*, 421*d*, 421*e*, and 421*f*, a plurality of links 422*a*, 422*b*, 422*c*, and 422*d* that are rotatably connected to each other by the joint portions 421*a* to 421*e*, and a holding unit 429 that is rotatably provided at a distal end of the arm portion 420 through the joint portion 421*f*. In addition, the holding unit 429 holds various medical instruments. In the exemplified drawing, a forceps 423 is attached to the holding unit 429.

The links 422a to 422d are bar-shaped members. One end of the link 422a is connected to the base portion 410 through the joint portion 421a. The other end of the link 422a is connected to one end of the link 422b through the joint portion 421b. Further, the other end of the link 422b is connected to one end of the link 422c through the joint portions 421c and 421d. Further, the other end of the link 422c is connected to one end of the substantially L-shaped link 422d through the joint portion 421e, and the other end of the link 422d and the holding unit 429 configured to hold the forceps 423 are connected through the joint portion 421f. In this manner, when ends of the plurality of links 422a to 422d are connected to each other by the joint portions 421a to 421f using the base portion 410 as a fulcrum, an arm shape extending from the base portion 410 is configured.

The forceps 423 corresponds to the above-described forceps 301 illustrated in FIG. 1. In FIG. 6, for simplicity of illustration, a specific shape of the forceps 423 is not illustrated, and a bar-shaped member is simply illustrated. However, actually, the end effector configured to grip or cut body tissues of the patient is provided at the distal end of the forceps 423. Positions and orientations of the arm portion 420 and the forceps 423 are controlled by the support arm device 400 such that the forceps 423 has a desired position and orientation with respect to body tissues of the patient when surgery is performed.

An actuator is provided in the joint portions 421a to 421f, and the joint portions 421a to 421f are rotatable with respect to a predetermined rotation axis by the actuator. The actuator may include a motor, an encoder and a torque sensor. The motor may correspond to the drive unit 211 illustrated in FIG. 5. The encoder and the torque sensor may correspond to the state detection unit 212 illustrated in FIG. 5.

When driving of the motors of the actuators of the joint portions 421a to 421f is controlled by the control device 440, driving of the arm portion 420, for example, extending or shortening (folding) the arm portion 420, is controlled. In this case, the control device 440 may compute a control amount of the motor of each of the actuators based on a state (that is, a state of the arm portion 420) of each of the joint portions 421a to 421f detected by the encoder and the torque sensor of the actuator.

Also, in the exemplified drawing, the support arm device 400 includes the six joint portions 421a to 421f, and implements 6 degrees of freedom for driving the arm portion 420. When the arm portion 420 is configured to have 6 degrees of freedom, it is possible to freely move the forceps 423 within a movable range of the arm portion 420. Accordingly, the forceps 423 can be inserted into the patient at various angles, and degrees of freedom increase when the forceps 423 is manipulated.

However, the configuration of the arm portion 420 is not limited to the exemplified drawing. The number and an arrangement of the joint portions 421a to 421f and the links 422a to 422d, and a direction of a drive shaft of the joint portions 421a to 421f may be appropriately set such that the arm portion 420 has a desired degree of freedom. However, in consideration of degrees of freedom of a position and an orientation of the forceps 423, the arm portion 420 may be appropriately configured to have 6 or more degrees of freedom.

When the arm portion 420 is operated, the surgeon inputs an instruction to the support arm device 400 through an input device (corresponds to the input device 220 illustrated in FIG. 5). A signal indicating the instruction input through the input device is transmitted to the control device 440. The control device 440 computes a control amount of the motor of the actuator of each of the joint portions 421a to 421f according to the instruction based on a state of each of the joint portions 421a to 421f detected by an encoder and a torque sensor of the actuator of each of the joint portions 421a to 421f. When the motor of each actuator is driven according to the computed control amount, the arm portion 420 is operated according to the instruction of the surgeon. In addition, when the forceps 423 includes a drive portion, similarly, a control amount of the motor configured to operate the drive portion is computed by the control device 440 based on the instruction input through the input device, the motor is driven according to the computed control amount, and thus the forceps 423 is operated according to the instruction of the surgeon. Note that communication between the input device and the control device 440 may be performed by various known wired or wireless methods.

The vibration detection module 10 is attached to the proximal end side of the forceps 423. Vibration generated in a distal end side of the forceps 423 is detected by vibration sensors (the first vibration sensor 120 and the second vibration sensor 130 illustrated in FIG. 5) of the vibration detection module 10. A signal indicating the vibration is transmitted to the control device 440. The control device 440 performs various types of processing (various types of processing corresponding to the vibration transmission unit 240 illustrated in FIG. 5) such as amplification and filtering on the signal, and transmits the signal to the input device in a hand of the surgeon. When a vibration presentation unit (corresponds to the vibration presentation unit 223 illustrated in FIG. 5) provided in the input device is driven according to the signal, vibration generated in the distal end side of the forceps 423 may be transmitted to the surgeon.

Note that communication between the vibration detection module 10 and the control device 440 may be performed by various known wired and wireless methods. In addition, a circuit board configured to perform a function of the vibration transmission unit 240 may be separated from the control device 440, and arranged near the vibration detection module 10. In this case, the vibration detection module 10 and the circuit board may be connected by a shorter wire. Accordingly, superimposition of noise before amplification by the amplifier in the signal indicating vibration detected by the vibration detection module 10 may be further suppressed.

4. Modification Examples

Some modification examples of the above-described embodiment will be described.

(4-1. Use of Vibration Detection Module for Damping Control)

As described above, in the support arm device 400, a position and an orientation of the forceps 423 are controlled by driving the arm portion 420. In this case, in the support arm device 400, in order to suppress vibration generated in the arm portion 420 according to movement of the arm portion 420, damping control may be performed. When damping control is performed, it is possible to determine a position of the forceps 423 with high precision, and increase operability for the surgeon.

In order to perform damping control, generally, a vibration sensor for damping control is provided in the arm portion 420 and/or the forceps 423, and damping control is performed based on a detection value of the vibration sensor.

In the present embodiment, the support arm device 400 may be configured such that damping control is performed based on a detection value of the vibration detection module 10. That is, the vibration detection module 10 may also perform a role of the vibration sensor for damping control. Accordingly, since damping control of the arm portion 420 can be performed without newly providing the vibration sensor for damping control, it is possible to perform damping control with lower costs and a simpler configuration.

(4-2. Other Application Examples of Vibration Detection Module)

In the above-described embodiment, as illustrated in FIG. 5, the vibration detection module 10 according to the present embodiment is applied to the surgical system 1 of a so-called master and slave method. However, the present embodiment is not limited thereto, but the vibration detection module 10 may be applied to other devices or systems.

For example, the vibration detection module 10 may be applied to the medical instrument that the surgeon directly holds and manipulates by hand. In the medical instrument that the surgeon directly manipulates, a manipulation unit such as a gripper for the surgeon to manipulate the medical instrument is provided in a proximal end side of the medical instrument. By directly manipulating the manipulation unit with his or her hand, the surgeon controls movement of the medical instrument. For example, in the case of the forceps, when the surgeon manipulates the manipulation unit provided in the proximal end side, an operation of the end effector at a distal end may be controlled. The vibration detection module 10 is attached to the proximal end side (for example, a portion that is slightly at a distal end side relative to the manipulation unit) of the medical instrument that is directly manipulated by the surgeon in this manner, and may detect vibration generated in the distal end side of the medical instrument. Note that, in this case, the tactile vibration presentation unit 225 of the vibration presentation unit 223 illustrated in FIG. 5 may be provided in the manipulation unit that is directly held by the surgeon such that vibration can be transmitted to a hand of the surgeon who manipulates the medical instrument.

In addition, for example, the vibration detection module 10 may be applied to a medical instrument provided in a device for surgery training. In this case, a history of vibration detected by the vibration detection module 10 in the device for training may be recorded in connection with the surgeon. When the recorded vibration history is analyzed, for example, it is possible to quantitatively acquire a difference between a characteristic of vibration generated in the medical instrument when a skilled person performs surgery and a characteristic of vibration generated in the medical instrument when a beginner performs surgery. In addition, it is possible to determine a proficiency level of the trained surgeon using the acquired vibration characteristic. In this case, an amount of damage that may occur in body tissues due to the medical instrument is quantitatively shown according to the characteristic of vibration. In addition, if practice is performed based on the characteristic of vibration generated when the skilled person performs surgery, the surgeon can become familiar with a surgery method of the skilled person more easily.

(4-3. Use of Detection Values of Other Vibration Sensors)

When a vibration sensor other than the first vibration sensor 120 and the second vibration sensor 130 of the vibration detection module 10 is attached to the forceps 423 and/or the arm portion 420 and a detection value of the other vibration sensor is used, it is possible to detect vibration using the vibration detection module 10 with higher precision. Note that the other vibration sensor may be provided in the housing 110 of the vibration detection module 10 as one component of the vibration detection module 10, or may be attached to the forceps 423 and/or the arm portion 420 as a separate member from the vibration detection module 10.

For example, the other vibration sensor may be arranged to be separated only a known interval from a proximal end side relative to the first vibration sensor 120 and the second vibration sensor 130 in a longitudinal direction of the forceps 423. When the first vibration sensor 120, the second vibration sensor 130 and the other vibration sensor are arranged in this manner, it is possible to separately detect vibration delivered from the distal end side and the forceps 423 and vibration delivered from a root side of the forceps 423 based on detection values of such vibration sensors. The vibration delivered from the root side of the forceps 423 is vibration caused by, for example, driving of the arm portion 420, and is vibration that is different from vibration that is normally intended to be detected and may become noise. Therefore, according to the configuration, it is possible to remove a component of vibration that may become noise and is delivered from the root side of the forceps 423 from vibration detected by the first vibration sensor 120 and the second vibration sensor 130. Therefore, it is possible to extract only a vibration component which is a vibration component that is normally intended to be obtained and is delivered from the distal end side of the forceps 423 and detect vibration generated in the distal end side of the forceps 423 with higher precision.

In addition, for example, the other vibration sensor may be arranged near a configuration that may be a noise source, for example, the motor of the actuator of the arm portion 420. Noise canceling is performed on vibration detected by the first vibration sensor 120 and the second vibration sensor 130 of the vibration detection module 10 using information about vibration detected by the other vibration sensor. Therefore, it is possible to more appropriately reduce a noise component and detect vibration generated in the distal end side of the forceps 423 with higher precision.

Note that a noise reduction process on vibration detected by the first vibration sensor 120 and the second vibration sensor 130 described above may be performed by, for example, the vibration transmission unit 240 illustrated in FIG. 5. In this case, in the vibration transmission unit 240, other than the components illustrated in FIG. 5, a noise reduction unit configured to perform various types of signal processing related to the noise reduction process may be provided. When the noise reduction unit is configured by a processor such as a CPU or a DSP, and the processor operates according to a predetermined program, predetermined signal processing related to the noise reduction process may be performed. Note that, since various known methods may be applied as a specific method of the noise reduction process, details thereof will be omitted herein.

In addition, for example, the force sensor may be provided as the other vibration sensor. That is, the vibration detection module 10 may further include the force sensor in addition to the first vibration sensor 120 (that is, an auditory sensor) and/or the second vibration sensor 130 (that is, a tactile sensor) as the vibration sensor. As described above in (1. Configuration of vibration detection module), in the present embodiment, the first vibration sensor 120 and the second vibration sensor 130 are used to detect vibration of a frequency band that is difficult to detect by the force sensor. Therefore, by further including the force sensor, in the vibration detection module 10, in addition to vibration of a frequency band corresponding to an auditory sense detected by the first vibration sensor 120 and/or vibration of a frequency band corresponding to a tactile sense detected by the second vibration sensor 130, vibration of a frequency band corresponding to a force detected by the force sensor can also be detected. In this manner, when the vibration detection module 10 is configured to further include the force sensor, it is possible to detect vibration of a wider frequency band by the vibration detection module 10 and increase detection sensitivity of vibration.

(4-4. Use of Directional Vibration Sensor)

As the first vibration sensor 120 and the second vibration sensor 130, a directional vibration sensor capable of extracting and detecting vibration delivered from a specific direction may be used. Accordingly, it is possible to appropriately detect only a vibration component delivered from the distal end side of the forceps 423 and detect vibration generated in the distal end side of the forceps 423 with higher precision.

(4-5. Number of Vibration Sensors Mounted on Vibration Detection Module)

In the above-described embodiment, the vibration detection module 10 includes the plurality of vibration sensors (the first vibration sensor 120 configured to detect auditory vibration and the second vibration sensor 130 configured to detect tactile vibration). However, the present embodiment is not limited thereto. As long as auditory vibration and tactile vibration can be detected, one vibration sensor may be mounted on the vibration detection module 10. For example, the vibration detection module 10 may be configured to include only one multi-axis acceleration sensor that can detect not only vibration of a frequency band corresponding to a tactile sense but also vibration of a frequency band corresponding to an auditory sense and has a wider range of detection as the vibration sensor. In this case, the one multi-axis acceleration sensor can also serve as the auditory sensor and the tactile sensor.

(4-6. Use of Information about Actuator Control)

As described above in (4-3. Use of detection values of other vibration sensors), the motor of the actuator provided in the arm portion 420 may serve as a noise source when vibration is detected by the vibration detection module 10. When vibration detected by the vibration detection module 10 is corrected using information about actuator control, it is possible to remove a noise component caused by driving of the motor of the actuator, and detect vibration generated in the distal end side of the forceps 423 with higher precision.

Specifically, for example, a relation between the number of revolutions of the motor of the actuator provided in the arm portion 420 and a characteristic (for example, a frequency) of vibration generated at that time is acquired in advance. Therefore, based on information about the number of revolutions of the motor when vibration is detected by the vibration detection module 10, information about a characteristic of vibration generated due to driving of the motor at that time is acquired. Noise canceling is performed on vibration detected by the vibration detection module 10 using information about the vibration characteristic. Accordingly, it is possible to remove a noise component caused by driving of the motor of the actuator from vibration detected by the vibration detection module 10.

The information about the number of revolutions of the motor of the actuator can be obtained from a control system configured to control driving of the actuator. For example, according to the surgical system 1 illustrated in FIG. 5, the information about the number of revolutions of the motor of the actuator may be provided from the control system 230 to the vibration transmission unit 240. Based on the information about the number of revolutions of the motor, the vibration transmission unit 240 can perform the noise canceling process described above and then transmit a signal indicating vibration to the input device 220. In this case, similarly to the above (4-3. Use of detection values of other vibration sensors), in the vibration transmission unit 240, instead of the configuration illustrated in FIG. 5, a noise reduction unit configured to perform signal processing related to the noise reduction process may be provided. Based on the information about the number of revolutions of the motor, the noise canceling process may be performed by the noise reduction unit.

(4-7. Other Methods of Presenting Vibration)

In the above-described embodiment, the vibration presentation unit includes an audio output device such as a speaker configured to transmit auditory vibration detected by the first vibration sensor 120 to the surgeon and a vibration element such as a voice coil configured to transmit tactile vibration detected by the second vibration sensor 130 to the surgeon. However, a method of presenting auditory vibration and tactile vibration to the surgeon is not limited thereto. Auditory vibration and tactile vibration may be presented to the surgeon by various methods that may be generally assumed as a method of transmitting vibration.

For example, the vibration presentation unit may include a display device configured to visually notify of information (for example, information indicating a characteristic such as a frequency) about detected auditory vibration and tactile vibration of the surgeon by text, a graph (waveform) and/or a color. The display device may be installed in the operating room, or mounted on a device that is worn by the surgeon when used such as a wearable device of an HMD or eyeglass type. In general, such a display device may be used to display, for example, an image of the operative portion imaged by the observation unit when surgery is performed while a state of the operative portion is observed by the observation unit such as an endoscope or a video microscope. That is, the image and information about auditory vibration and tactile vibration may also be displayed on the display device configured to display the image of the operative portion imaged by the observation unit such as the endoscope.

Here, as described above in (1. Configuration of vibration detection module), tactile vibration may include surface texture information or rigidity information of body tissues in contact with the forceps 423. When the vibration element is used as the vibration presentation unit, the surgeon can intuitively tactilely recognize such information by the vibration element, but it may be useful for such information to be notified of more explicitly through visual and/or auditory methods. For example, when it is determined that a state or rigidity (elasticity) of a surface of body tissues currently in contact with the forceps 423 is different from a normal state or rigidity based on a characteristic of tactile vibration, the surgeon may be notified of information to that effect through visual and/or auditory methods such as text and/or audio. For example, when a lesioned part to be resected and a normal part have a different surface state or rigidity, the surgeon is notified of the information through visual and/or auditory methods. Therefore, the surgeon can recognize a possibility of the forceps 423 currently in contact with the lesioned part more clearly.

5. Supplement

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to an embodiment of the present disclosure can exhibit other effects that are evident to those skilled in the art along with or instead of the effects based on the present specification.

(1)

A medical apparatus, including:

medical vibration detection circuitry that is detachable from a medical instrument at an attachment position of the medical instrument in a longitudinal direction and that is configured to detect vibration generated in a distinct portion of the medical instrument, the distinct portion including at least a portion disposed toward a distal end of the medical instrument from the attachment position.

(2)

The medical apparatus according to (1), wherein the distinct portion includes at least a portion of the medical instrument between a distal end and the attachment position.

(3)

The medical apparatus according to (1)-(2), wherein the vibration detection circuitry is attached to a proximal side of the medical instrument which is a side at which the medical instrument is supported, and is configured to detect vibration generated in the medical instrument in a distal side that approaches or comes into contact with a body tissue of a patient.

(4)

The medical apparatus according to (1)-(3), wherein the medical vibration detection circuitry includes:

a housing, and one or a plurality of vibration sensors disposed in the housing, wherein the one or plurality of vibration sensors detect at least one of vibration in a frequency band corresponding to an auditory sense and vibration in a frequency band corresponding to a tactile sense.

(5)

The medical apparatus according to (1)-(4), wherein a seal that seals the housing is provided in a gap between an inside and an outside of the housing.

(6)

The medical apparatus according to (1)-(5), wherein the one or plurality of vibration sensors include at least one of an auditory sensor that detects vibration in a frequency band corresponding to an auditory sense and a tactile sensor that detects vibration in a frequency band corresponding to a tactile sense.

(7)

The medical apparatus according to (1)-(6), wherein the vibration sensor further includes a force sensor that detects vibration in a frequency band corresponding to a force sense.

(8)

The medical apparatus according to (1)-(7), wherein the auditory sensor is a microphone and the tactile sensor is an acceleration sensor.

(9)

The medical apparatus according to (1)-(8), wherein the vibration detection circuitry is further configured to output a signal representing the vibration detected by the vibration detection circuitry to provide feedback of the vibration to a surgeon who manipulates the medical instrument through a vibration sensitive human-machine interface.

(10)

The medical apparatus according to (1)-(9), wherein the vibration sensitive human-machine interface includes an audio output device that outputs detected vibration at a frequency band corresponding to an auditory sense as audio and a vibrator that performs vibration according to detected vibration at a frequency band corresponding to a tactile sense.

(11)

The medical apparatus according to (1)-(10), wherein the vibration sensitive human-machine interface presents information about the detected vibration to a surgeon.

(12)

The medical apparatus according to (1)-(11), wherein the vibration sensitive human-machine interface presents, to the surgeon, at least one of surface texture information of a body tissue of a patient in contact with the medical instrument and rigidity information of the body tissue, the surface texture information and the rigidity information being obtained based on the detected vibration.

(13)

The medical apparatus according to (1)-(12), wherein the medical instrument is supported by an arm portion of a support arm device, wherein the support arm device operates according to an instruction by a surgeon through an input device that is installed separately from the support arm device, and wherein the vibration detection circuitry is configured to output a signal representing the vibration detected by the vibration detection circuitry to provide feedback of the vibration to the surgeon through a vibration sensitive human-machine interface provided in the input device.

(14)

The medical apparatus according to (1)-(13), wherein a force sensor that detects a force applied to the arm portion is provided in the arm portion, and wherein the vibration detection circuitry is configured to output a signal representing the force that is detected by the force sensor and applied to the medical instrument to provide feedback of the force to the surgeon through the input device.

(15)

The medical apparatus according to (1)-(14), wherein a vibration sensor used for noise reduction and that detects vibration generated from a motor of an actuator provided in a joint portion of the arm portion, is provided in the arm portion, and wherein a component of vibration, generated by the motor, is removed from vibration detected by the vibration detection circuitry using a detection value from the vibration sensor used for noise reduction.

(16)

The medical apparatus according to (1)-(15), wherein the vibration detected by the vibration detection circuitry is used for damping control of the arm portion.

(17)

The medical apparatus according to (1)-(16), wherein the medical vibration detection circuitry includes:

a housing, and a plurality of vibration sensors arranged in the housing in parallel at predetermined intervals in a longitudinal direction of the medical instrument, wherein vibration delivered from a distal side of the medical instrument and vibration delivered from a proximal side of the medical instrument are separately detected by the plurality of vibration sensors.

(18)

The medical apparatus according to (1)-(17), wherein the medical vibration detection circuitry includes:

a housing, and one or a plurality of vibration sensors disposed in the housing, wherein the one or a plurality of vibration sensors is a directional vibration sensor that detects vibration delivered from a predetermined direction, and wherein the one or a plurality of vibration sensors is disposed to detect vibration delivered from a distal side of the medical instrument.

(19)

The medical apparatus according to (1)-(18), wherein the vibration detection circuitry is attached to the medical instrument provided in a surgery training device and detects vibration generated in the medical instrument when training is performed.

(20)

A medical apparatus vibration detection method, including:

attaching vibration detection circuitry that is detachable from a medical instrument at an attachment position of the medical instrument in a longitudinal direction; and detecting, by the vibration detection circuitry, vibration generated in a distinct portion of the medical instrument, the distinct portion including at least a portion of the medical instrument disposed toward a distal end of the medical instrument from the attachment position.

(21)

A surgical system including:

a medical instrument;

a support arm device that supports the medical instrument; and medical vibration detection circuitry that is detachable from a medical instrument at an attachment position of the medical instrument in a longitudinal direction and that is configured to detect vibration generated in a distinct portion of the medical instrument, the distinct portion including at least a portion of the medical instrument disposed toward a distal end of the medical instrument from the attachment position.

(22)

A vibration detection module that is detachable from a portion of a long medical instrument in a longitudinal direction and detects vibration generated in another portion of the medical instrument in the longitudinal direction separated from an attachment position.

(23)

The vibration detection module according to (22), wherein the vibration detection module is attached to a proximal end side which is a side in which the medical instrument is supported, and detects vibration generated in the medical instrument in a distal end side that approaches or comes into contact with a body tissue of a patient.

(24)

The vibration detection module according to (22) or (23), including:

a housing; and one or plurality of vibration sensors disposed in the housing, wherein the vibration sensor detects at least one of vibration of a frequency band corresponding to an auditory sense and vibration of a frequency band corresponding to a tactile sense.

(25)

The vibration detection module according to (24), wherein a sealing member configured to seal the housing is provided in a gap that spatially connects an inside and an outside of the housing.

(26)

The vibration detection module according to (24) or (25), wherein the vibration sensor includes at least one of an auditory sensor configured to detect vibration of a frequency band corresponding to an auditory sense and a tactile sensor configured to detect vibration of a frequency band corresponding to a tactile sense.

(27)

The vibration detection module according to (26), wherein the vibration sensor further includes a force sensor configured to detect vibration of a frequency band corresponding to a force sense.

(28)

The vibration detection module according to (26), wherein the auditory sensor is a microphone and the tactile sensor is an acceleration sensor.

(29)

The vibration detection module according to any one of (22) to (28), wherein the vibration detected by the vibration detection module is transmitted to a surgeon who manipulates the medical instrument through a vibration presentation unit.

(30)

The vibration detection module according to (29), wherein the vibration presentation unit includes an audio output device configured to output detected vibration of a frequency band corresponding to an auditory sense as audio and a vibration element configured to perform vibration according to detected vibration of a frequency band corresponding to a tactile sense.

(31)

The vibration detection module according to (29) or (30), wherein the vibration presentation unit includes a display device configured to visually notify the surgeon of information about the detected vibration.

(32)

The vibration detection module according to (31), wherein the display device notifies the surgeon of at least one of surface texture information of a body tissue of a patient in contact with the medical instrument and rigidity information of the body tissue, the surface texture information and the rigidity information being obtained based on the detected vibration.

(33)

The vibration detection module according to any one of (22) to (32), wherein the medical instrument is supported by an arm portion of a support arm device, wherein the arm portion and the medical instrument are operated according to an instruction by a surgeon through an input device that is installed separately from the support arm device, and wherein the vibration detected by the vibration detection module is transmitted to the surgeon through a vibration presentation unit provided in the input device.

(34)

The vibration detection module according to (33), wherein a force sensor configured to detect a force applied to the arm portion is provided in the arm portion, and wherein the force that is detected by the force sensor and applied to the medical instrument is transmitted to the surgeon through the input device.

(35)

The vibration detection module according to (33) or (34), wherein a vibration sensor for noise reduction configured to detect vibration generated from a motor of an actuator provided in a joint portion of the arm portion is provided in the arm portion, and wherein a component of vibration generated by the motor is removed from vibration detected by the vibration detection module using a detection value by the vibration sensor for noise reduction, and then vibration from which the component of the vibration has been removed is transmitted to the surgeon.

(36)

The vibration detection module according to any of (33) to (35), wherein, using a relation between the number of revolutions of the motor of the actuator provided in joint portions of the arm portion and vibration generated by the motor, based on information about the number of revolutions of the motor while the arm portion is operated, a component of vibration generated by the motor is removed from vibration detected by the vibration detection module, and then vibration from which the component of the vibration has been removed is transmitted to the surgeon.

(37)

The vibration detection module according to any one of (33) to (36), wherein the vibration detected by the vibration detection module is used for damping control of the arm portion.

(38)

The vibration detection module according to any one of (22) to (37), including:

a housing; and a plurality of vibration sensors arranged in the housing in parallel at predetermined intervals in a longitudinal direction of the medical instrument, wherein vibration delivered from a distal end side of the medical instrument and vibration delivered from a proximal end side of the medical instrument are separately detected by the plurality of vibration sensors.

(39)

The vibration detection module according to any one of (22) to (38), including:

a housing; and one or a plurality of vibration sensors disposed in the housing, wherein the vibration sensor is a directional vibration sensor capable of extracting and detecting vibration delivered from a predetermined direction, and wherein the vibration sensor is disposed to extract and detect vibration delivered from a distal end side of the medical instrument.

(40)

The vibration detection module according to any one of (22) to (39), wherein the vibration detection module is attached to the medical instrument provided in a device for surgery training and detects vibration generated in the medical instrument when training is performed.

(41)

A vibration detection method including:

attaching a vibration detection module detachable from a long medical instrument to a portion of the medical instrument in a longitudinal direction and detecting, by the vibration detection module, vibration generated in another portion of the medical instrument in the longitudinal direction separated from an attachment position.

(42)

A surgical system including:

a long medical instrument used for a patient;

a support arm device configured to support the medical instrument; and a vibration detection module that is detachable from a portion of the medical instrument in a longitudinal direction, and detects vibration generated in another portion of the medical instrument in the longitudinal direction separated from an attachment position.

REFERENCE SIGNS LIST 1 surgical system
10 vibration detection module
110 housing
120 first vibration sensor
130 second vibration sensor
140 sealing member
150 cable
210, 400 support arm device
211 drive unit
212 state detection unit
220 input device
221 input unit
222 power presentation unit
223 vibration presentation unit
224 auditory vibration presentation unit
225 tactile vibration presentation unit
230 control system
240 vibration transmission unit
301, 423 forceps
303, 420 arm portion
410 base portion
421a to 421f joint portion
422a to 422d link
429 holding unit
440 control device

The invention claimed is:

1. A medical apparatus, comprising:
medical vibration detection circuitry included in a housing that is detachable from a medical instrument at an attachment position of the medical instrument, that is attached in a longitudinal direction, and that is configured to detect vibration generated in a distinct portion of the medical instrument, the distinct portion including at least a portion disposed toward a distal end of the medical instrument from the attachment position,
wherein the housing has two sides each side having an opening through which the medical instrument passes.

2. The medical apparatus according to claim 1,
wherein the distinct portion includes at least a portion of the medical instrument between the distal end and the attachment position.

3. The medical apparatus according to claim 1,
wherein the vibration detection circuitry is attached to a proximal side of the medical instrument which is a side at which the medical instrument is supported, and is configured to detect vibration generated in the medical instrument in a distal side that approaches or comes into contact with a body tissue of a patient.

4. The medical apparatus according to claim 1, wherein the medical vibration detection circuitry includes:
one or a plurality of vibration sensors disposed in the housing,
wherein the one or plurality of vibration sensors detect at least one of vibration in a frequency band corresponding to an auditory sense and vibration in a frequency band corresponding to a tactile sense.

5. The medical apparatus according to claim 4,
wherein a seal that seals the housing is provided in a gap between an inside and an outside of the housing.

6. The medical apparatus according to claim 4,
wherein the one or plurality of vibration sensors include at least one of an auditory sensor that detects vibration in a frequency band corresponding to an auditory sense and a tactile sensor that detects vibration in a frequency band corresponding to a tactile sense.

7. The medical apparatus according to claim 6,
wherein the vibration sensor further includes a force sensor that detects vibration in a frequency band corresponding to a force sense.

8. The medical apparatus according to claim 6,
wherein the auditory sensor is a microphone and the tactile sensor is an acceleration sensor.

9. The medical apparatus according to claim 1,
wherein the vibration detection circuitry is further configured to output a signal representing the vibration detected by the vibration detection circuitry to provide feedback of the vibration to a surgeon who manipulates the medical instrument through a vibration sensitive human-machine interface.

10. The medical apparatus according to claim 9,
wherein the vibration sensitive human-machine interface includes an audio output device that outputs detected vibration at a frequency band corresponding to an auditory sense as audio and a vibrator that performs vibration according to detected vibration at a frequency band corresponding to a tactile sense.

11. The medical apparatus according to claim 10,
wherein the vibration sensitive human-machine interface presents information about the detected vibration to a surgeon.

12. The medical apparatus according to claim 11,
wherein the vibration sensitive human-machine interface presents, to the surgeon, at least one of surface texture information of a body tissue of a patient in contact with the medical instrument and rigidity information of the body tissue, the surface texture information and the rigidity information being obtained based on the detected vibration.

13. The medical apparatus according to claim 1,
wherein the medical instrument is supported by an arm portion of a support arm device,
wherein the support arm device operates according to an instruction by a surgeon through an input device that is installed separately from the support arm device, and
wherein the vibration detection circuitry is configured to output a signal representing the vibration detected by the vibration detection circuitry to provide feedback of the vibration to the surgeon through a vibration sensitive human-machine interface provided in the input device.

14. The medical apparatus according to claim 13,
wherein a force sensor that detects a force applied to the arm portion is provided in the arm portion, and
wherein the vibration detection circuitry is configured to output a signal representing the force that is detected by the force sensor and applied to the medical instrument to provide feedback of the force to the surgeon through the input device.

15. The medical apparatus according to claim 13,
wherein a vibration sensor used for noise reduction and that detects vibration generated from a motor of an actuator provided in a joint portion of the arm portion, is provided in the arm portion, and
wherein a component of vibration, generated by the motor, is removed from vibration detected by the vibration detection circuitry using a detection value from the vibration sensor used for noise reduction.

16. The medical apparatus according to claim 13,
wherein the vibration detected by the vibration detection circuitry is used for damping control of the arm portion.

17. The medical apparatus according to claim 1, wherein the medical vibration detection circuitry includes:
a plurality of vibration sensors arranged in the housing in parallel at predetermined intervals in a longitudinal direction of the medical instrument,
wherein vibration delivered from a distal side of the medical instrument and vibration delivered from a proximal side of the medical instrument are separately detected by the plurality of vibration sensors.

18. The medical apparatus according to claim 1, wherein the medical vibration detection circuitry includes:
one or a plurality of vibration sensors disposed in the housing,
wherein the one or a plurality of vibration sensors is a directional vibration sensor that detects vibration delivered from a predetermined direction, and
wherein the one or a plurality of vibration sensors is disposed to detect vibration delivered from a distal side of the medical instrument.

19. The medical apparatus according to claim 1,
wherein the vibration detection circuitry is attached to the medical instrument provided in a surgery training device and detects vibration generated in the medical instrument when training is performed.

20. The medical apparatus according to claim 1, wherein the housing completely surrounds the medical instrument at the attachment position.

21. The medical apparatus according to claim 1, wherein a component of vibration, generated by a motor, is removed from vibration detected by the vibration detection circuitry.

22. A medical apparatus vibration detection method, comprising:
attaching vibration detection circuitry included in a housing that is detachable from a medical instrument at an attachment position of the medical instrument and that is attached in a longitudinal direction; and
detecting, by the vibration detection circuitry, vibration generated in a distinct portion of the medical instrument, the distinct portion including at least a portion of the medical instrument disposed toward a distal end of the medical instrument from the attachment position,
wherein the housing has two sides each side having an opening through which the medical instrument passes.

23. A surgical system comprising:
a medical instrument;
a support arm device that supports the medical instrument; and
medical vibration detection circuitry included in a housing that is detachable from the medical instrument at an attachment position of the medical instrument, that is attached in a longitudinal direction, and that is configured to detect vibration generated in a distinct portion of the medical instrument, the distinct portion including at least a portion of the medical instrument disposed toward a distal end of the medical instrument from the attachment position, wherein the housing has two opposite sides each side having an opening through which the medical instrument passes.

\* \* \* \* \*